United States Patent [19]
Talonn et al.

[11] Patent Number: 5,088,988
[45] Date of Patent: Feb. 18, 1992

[54] COMBINED DENTAL SYRINGE AND NEEDLE SHIELD

[75] Inventors: Daniel A. Talonn, University City; Alan B. Ranford, St. Louis, Mo.

[73] Assignee: Sherwood Medical Company, St. Louis, Mo.

[21] Appl. No.: 471,995

[22] Filed: Jan. 29, 1990

Related U.S. Application Data

[63] Continuation-in-part of Ser. No. 212,528, Jun. 28, 1988, Pat. No. 5,053,018.

[51] Int. Cl.$^5$ .............................................. A61M 5/32
[52] U.S. Cl. ................................... 604/198; 604/263; 604/232
[58] Field of Search ............... 604/192, 198, 218, 232, 604/234, 263, 110, 195, 197; 128/919

[56] References Cited

U.S. PATENT DOCUMENTS

| | | | |
|---|---|---|---|
| 2,571,653 | 10/1951 | Bastien . | |
| 2,935,067 | 5/1960 | Bouet | 128/216 |
| 2,956,563 | 10/1960 | Sarnoff | 604/232 |
| 3,046,985 | 7/1962 | Saenz | 128/218 |
| 3,134,380 | 5/1964 | Armao | 128/215 |
| 3,556,099 | 1/1971 | Knight | 604/232 |
| 3,780,734 | 12/1973 | Wulff | 128/218 R |
| 3,890,971 | 6/1975 | Leeson et al. | 128/218 R |
| 4,139,009 | 2/1979 | Alvarez | 128/218 N |
| 4,356,822 | 11/1982 | Winstead-Hall | 128/215 |
| 4,425,120 | 1/1984 | Sampson et al. | 604/198 |
| 4,573,976 | 3/1986 | Sampson et al. | 604/198 |
| 4,631,057 | 12/1986 | Mitchell | 604/198 |
| 4,643,200 | 2/1987 | Jennings, Jr. | 128/763 |
| 4,650,468 | 3/1987 | Jennings, Jr. | 604/110 |
| 4,655,751 | 4/1987 | Harbaugh | 604/198 |
| 4,666,435 | 5/1987 | Braginetz | 604/198 |
| 4,681,567 | 7/1987 | Master et al. | 604/198 |
| 4,693,708 | 9/1987 | Wanderer et al. | 604/198 |
| 4,695,274 | 9/1987 | Fox | 604/198 |
| 4,702,738 | 10/1987 | Spencer | 604/198 |
| 4,723,943 | 2/1988 | Spencer | 604/198 |
| 4,731,059 | 3/1988 | Wanderer et al. | 604/192 |
| 4,737,144 | 4/1988 | Choksi | 604/198 |
| 4,743,233 | 5/1988 | Schneider | 604/192 |
| 4,747,837 | 5/1988 | Hauck | 604/198 |
| 4,758,231 | 7/1988 | Haber et al. | 604/198 |
| 4,767,413 | 8/1988 | Haber et al. | 604/198 |
| 4,772,272 | 9/1988 | McFarland | 604/198 |
| 4,782,841 | 11/1988 | Lopez | 128/164 |
| 4,790,828 | 12/1988 | Dombrowski et al. | 604/198 |
| 4,790,828 | 12/1988 | Dombrowski et al. | 604/198 |
| 4,801,295 | 1/1989 | Spencer | 604/198 |
| 4,810,248 | 3/1989 | Masters et al. | 604/192 |
| 4,813,426 | 3/1989 | Haber et al. | 128/763 |
| 4,820,275 | 4/1989 | Haber et al. | 604/198 |
| 4,840,185 | 6/1989 | Hernandez | 128/763 |
| 4,842,587 | 6/1989 | Poncy | 604/198 |
| 4,871,355 | 10/1989 | Kikkawa | 604/198 |

(List continued on next page.)

FOREIGN PATENT DOCUMENTS

| | | | |
|---|---|---|---|
| 0331452 | 9/1989 | European Pat. Off. | 604/198 |
| 9000073 | 1/1990 | World Int. Prop. O. | 604/263 |

Primary Examiner—C. Fred Rosenbaum
Assistant Examiner—Mark O. Polutta
Attorney, Agent, or Firm—Andrew J. Beck; Montgomery W. Smith; Richard D. Allison

[57] ABSTRACT

A safety dental syringe of the type adapted to receive a medication cartridge therein but having a protective needle shield thereon which is movable between a retracted position wherein the needle is exposed and a locked and extended position wherein the needle is protected and the needle shield is prevented from returning to the retracted position. A collar is attached to the distal end of the dental syringe to selectively engage a key on the needle shield as the needle shield is moved between the retracted and extended positions. The needle shield slides longitudinally between the retracted and extended positions and may be rotated about the barrel of the dental syringe to lock the needle shield in the locked and extended position. A locking mechanism is disclosed which preferably includes a series of ramps and slots adapted to engage portions of the keys on the needle shield to retain the needle shield in the locked and extended position.

35 Claims, 6 Drawing Sheets

U.S. PATENT DOCUMENTS

| | | | |
|---|---|---|---|
| 4,874,383 | 10/1989 | McNaughton | 604/198 |
| 4,915,701 | 4/1990 | Halkyard | 604/198 |
| 4,923,445 | 5/1990 | Ryan | 604/195 |
| 4,927,018 | 5/1990 | Yang et al. | 206/365 |
| 4,929,237 | 5/1990 | Medway | 604/198 |
| 4,935,016 | 6/1990 | Deleo | 604/198 |
| 4,994,045 | 2/1991 | Ranford | 604/198 |
| 4,998,920 | 3/1991 | Johnson | 604/198 |
| 4,998,924 | 3/1991 | Ranford | 604/798 |
| 5,011,479 | 4/1991 | Le et al. | 604/198 |
| 5,019,051 | 5/1991 | Hake | 604/198 |
| 5,024,616 | 6/1991 | Ogle, II | 604/192 |
| 5,024,660 | 6/1991 | McNaughton | 604/110 |
| 5,045,066 | 9/1991 | Scheuble et al. | 604/198 |

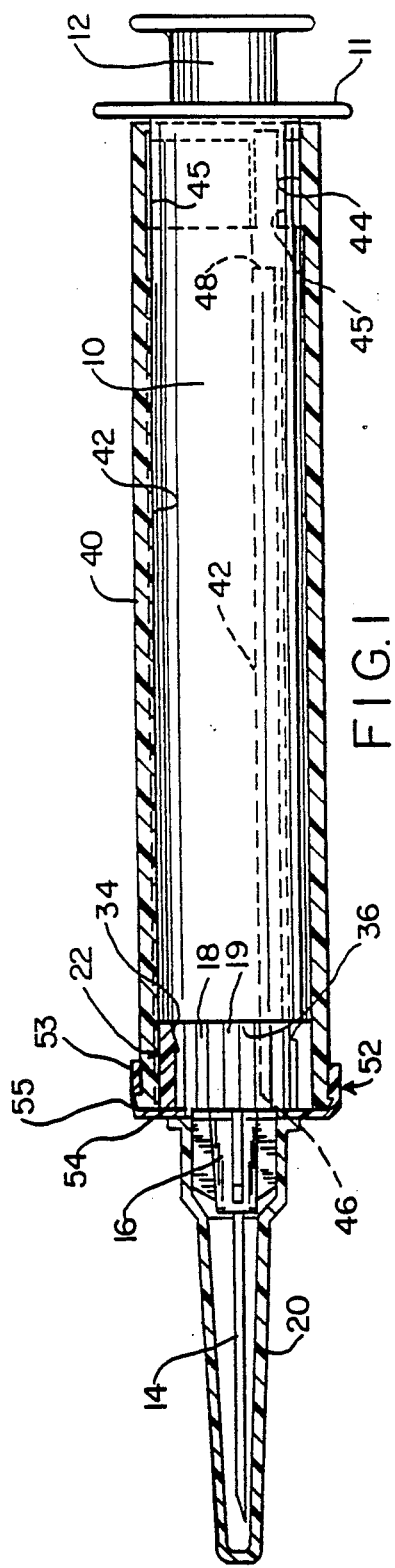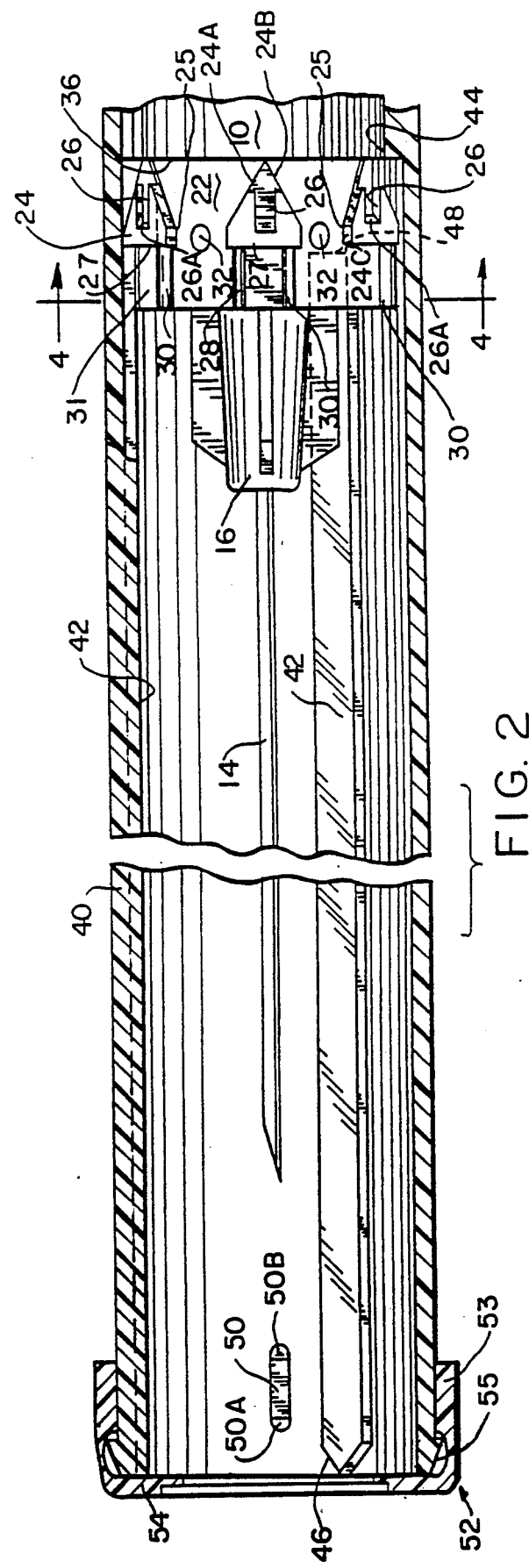

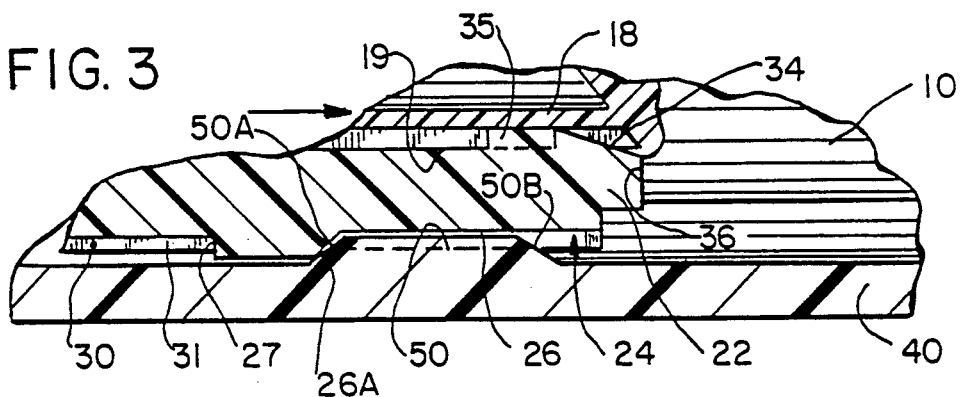
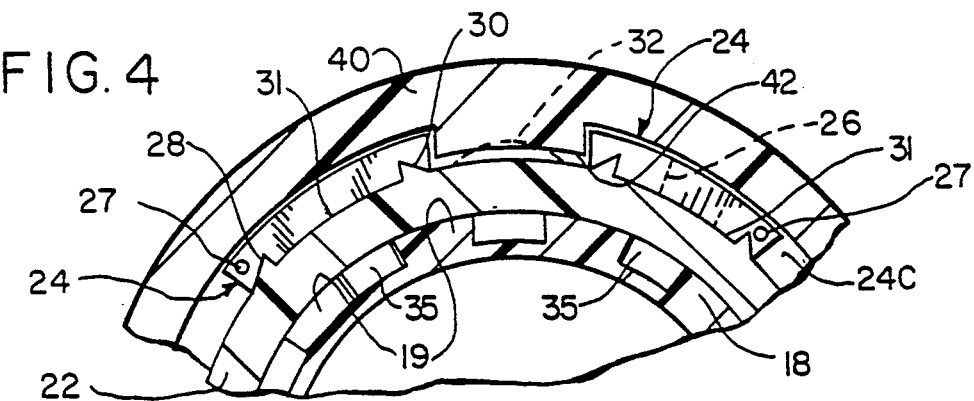
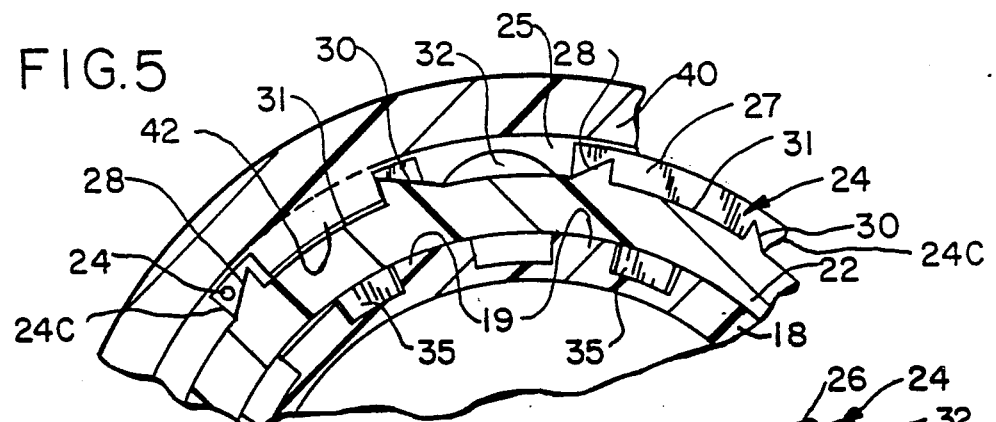
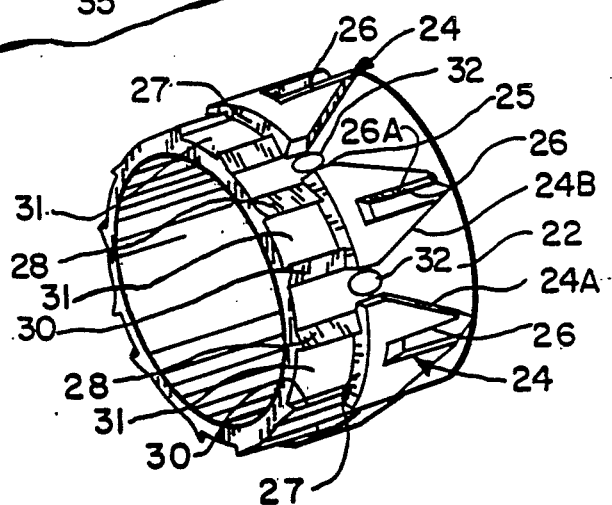

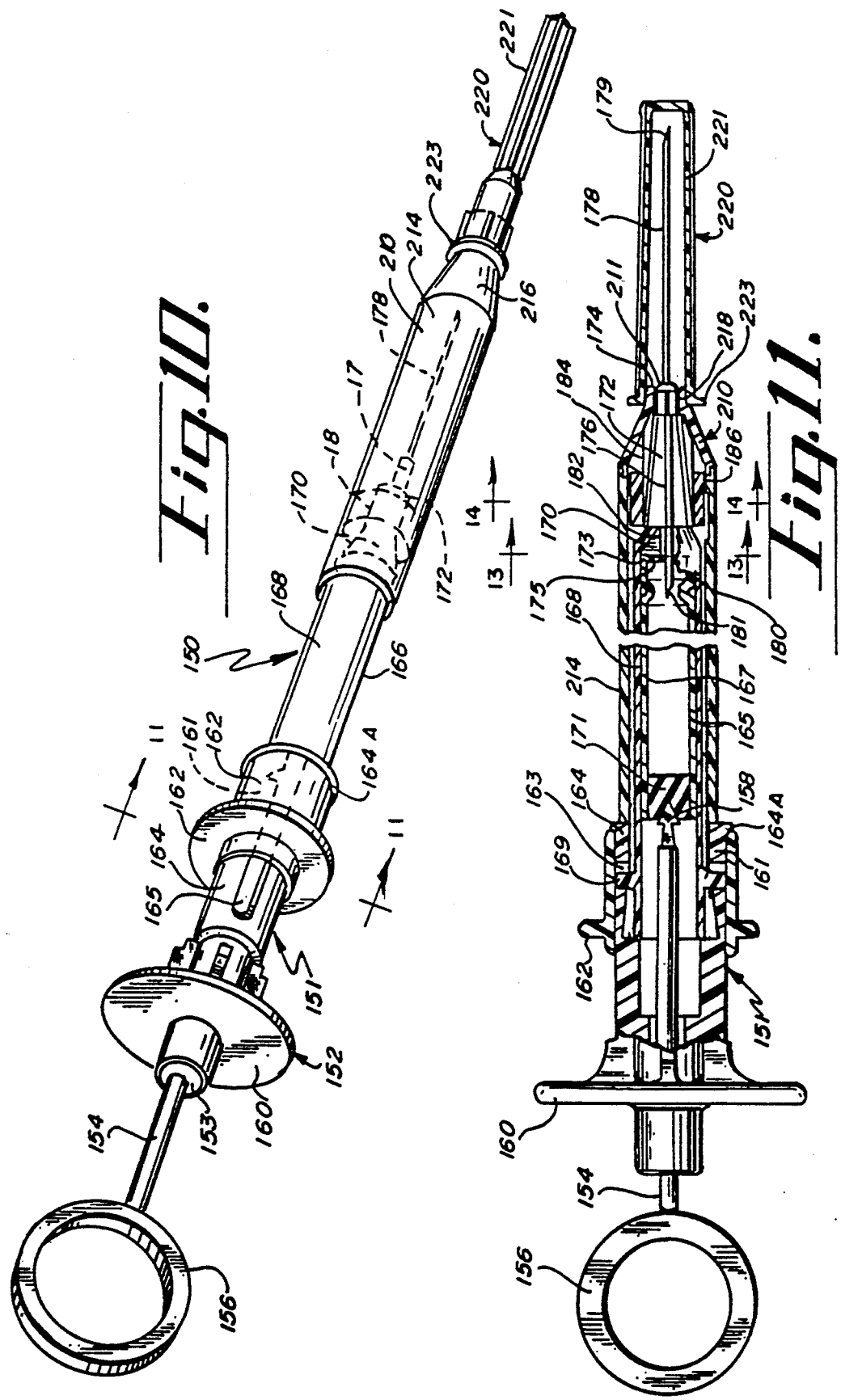

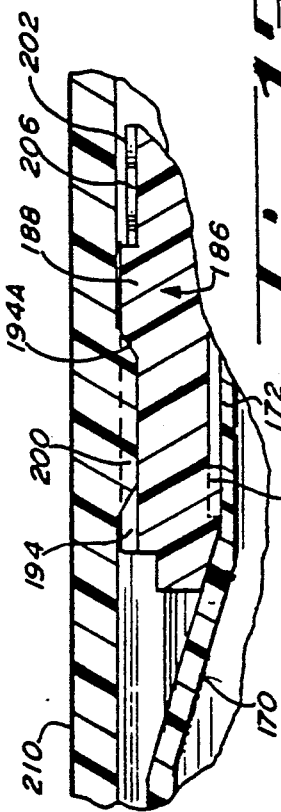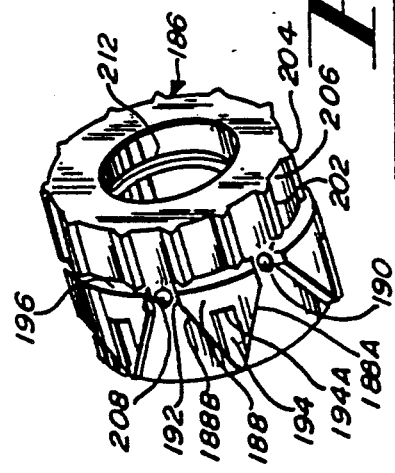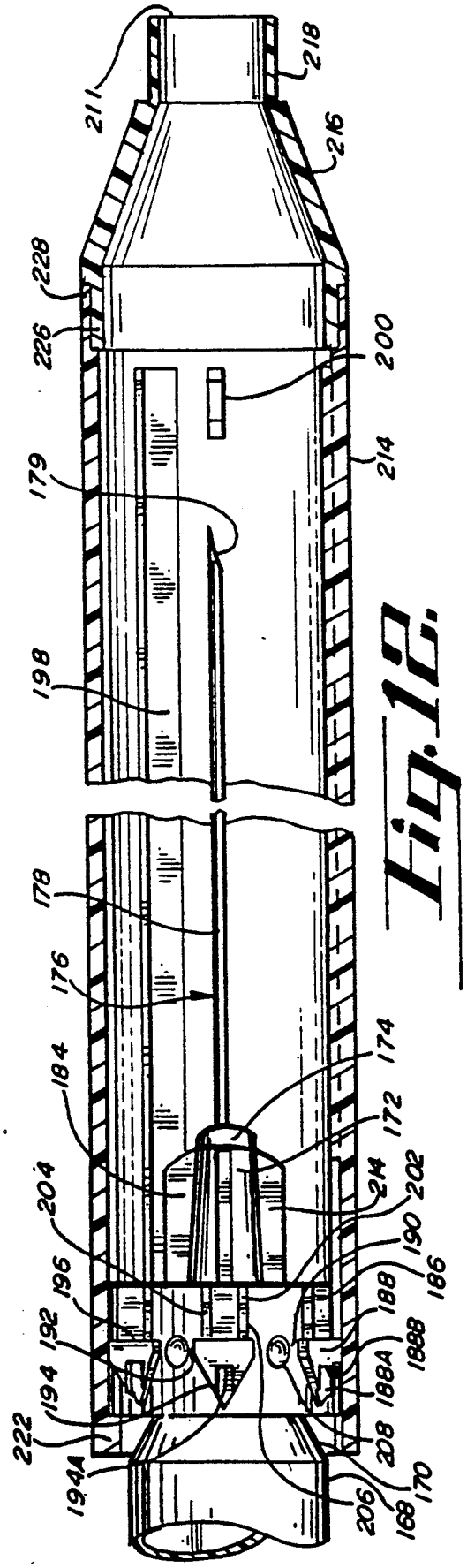

COMBINED DENTAL SYRINGE AND NEEDLE SHIELD

RELATED U.S. PATENT INFORMATION

This application is a continuation-in-part of a copending application filed on June 28, 1988, designated as U.S. patent application Ser. No. 212,528, now U.S. Pat. No. 5,053,018 these applications being commonly assigned to Sherwood Medical Company.

FIELD OF THE INVENTION

This invention relates to syringes and, in particular, to a conventional dental syringe of the type adapted to receive a medication-containing cartridge therein but having a novel extendable needle shield primarily for the purpose of preventing or minimizing accidental needle sticks.

BACKGROUND OF THE INVENTION

Most syringes used today for medical, laboratory or dental purposes are sold as disposable items intended to be used only once. Disposal of such syringes has posed a safety hazard for the individuals who use the syringes as well as for those who dispose of them. With the onset of AIDS, the concern for infection due to accidental needle sticks from used syringes has increased and a number of different devices have been proposed to minimize the possibility of spreading infectious disease due to accidents of this type.

One approach to this problem is to provide an extendable needle shield which, after the syringe has been used, can be pushed to an extended position where it covers the needle, making it difficult for an individual to accidentally contact the needle. A common feature of such constructions is that when the needle shield is pushed to its extended position, it is locked so that it cannot be retracted (thus exposing the needle) except by application of extraordinary force.

A number of such constructions have been proposed to satisfy the general requirement that the needle be permanently covered after the syringe has been used. Some of these constructions involve complex locking mechanisms and, in others, locking occurs automatically when the shield is fully extended. These known devices satisfy many of the functional requirements of a needle shield but require, in most cases, modification of the standard syringe construction. This is highly undesirable for many manufacturers because of the sizable investment they may have already made in their existing molding equipment for producing the syringes.

Constructions have also been proposed which include an opening or slot in the side of the shield. This is undesirable because the needle can extend through the opening if the needle or the needle shield is deflected when the needle shield is in the extended position. Other proposed devices include open ended needle shields which may not block access to the needle point by small fingers.

Those devices which lock in response to axial movement of the needle shield to the extended position, (i.e., without any rotation) have certain inherent drawbacks that result primarily from the requirement that substantial force be exerted axially to lock the shield in its extended position. In the first place, the likelihood of unintentional and irreversible locking is greater with such devices than with those devices which require rotation to lock. Also, in certain constructions, it may be difficult to verify that the needle shield is locked upon extension without attempting to retract the shield, which increases the possibility of unintended exposure of the needle.

In addition to the design requirements described above, the design of this type of dental syringe must allow for the insertion of a medication cartridge through the proximal end of the dental syringe. Additionally, the outer diameter of the distal end of the needle shield should be minimized so that the dentist is able to better observe the needle of the dental syringe during the use thereof and so that the distal end of the needle shield does not interfere with the placement or use of other instruments which may simultaneously be present in the patient's mouth.

Accordingly, it is an object of this invention to provide a protective needle shield of the type described above which can be added at minimal expense to conventional hypodermic or dental syringes.

Another object of the present invention is to provide a relatively inexpensive protective shield which satisfies the functional requirements of a needle shield and includes none of the drawbacks mentioned above.

Another object of the present invention is to provide an extendable needle shield for a dental syringe which performs all of the necessary functions of such a shield and which is particularly well suited to an automated process of manufacture.

A further object of the present invention is to provide an extendable needle shield for a standard hypodermic or dental syringe which is improved both from the points of view of functional utility and cost of manufacture.

A still further object of the present invention is to provide an inexpensive method of assembling a protective needle shield and dental syringe.

SUMMARY OF THE INVENTION

In accordance with the invention, a needle shield is mounted coaxially on a syringe barrel. The needle shield includes one or more elongated keys on its inner surface. A collar is provided on the distal end of the barrel adjacent to the needle or needle hub. The collar may be a separate part or it may be integrally formed with the barrel and includes on its outer surface at least one locking slot. The key slides in a path outside of the locking slot and can be rotated into the locking slot when the needle shield is extended. Both the collar and shield can be molded from plastic materials so that the cost of the shield is relatively low.

In the preferred embodiment, the needle shield includes a plurality of elongated locking keys and the collar includes a plurality of locking slots. Each locking slot is defined by opposing walls, at least one of which includes a ramp over which the keys can ride when the shield is in its extended position and subsequently rotated to an extended and locked position. As the keys are rotated into the locking slots, rearward movement of the needle shield to its retracted position is prevented by a surface on the collar at the back of each locking slot.

In accordance with one feature of the present invention, protrusions on the collar and the forward portions of the keys are shaped such that during assembly the keys are directed into keyways formed between the locking slots as the collar is moved relative to the needle shield. Thus, the construction is well suited to an automated process in which the collar and needle shield are secured to the standard hypodermic or dental syringe by machine.

A further feature of the present invention is the provision of a needle shield having a reduced diameter distal end to allow for the attachment of a needle protecting needle sheath thereon.

Other features of the present invention are set forth hereinafter in the detailed description of the preferred embodiments.

IN THE DRAWINGS

FIG. 1 is a side elevational view, partly in section, showing a needle shield and collar in accordance with a preferred embodiment of the invention secured to a conventional hypodermic syringe with the needle shield in its retracted position;

FIG. 2 is an enlarged sectional view with the needle shield in cross-section in its extended position;

FIG. 3 is a further enlarged partial side sectional view showing details of the collar and needle shield;

FIG. 4 is a sectional view along the line 4—4 of FIG. 2 with the needle shield pulled to its extended position but before rotation;

FIG. 5 is a sectional view along the line 4—4 of FIG. 2 showing the needle shield rotated into its locked position;

FIG. 6 and 7 are perspective views of a preferred embodiment of the collar;

FIG. 10 is a perspective view of an alternate embodiment of the present invention shown mounted on a conventional dental syringe with the needle shield in the extended position;

FIG. 11 is a side elevation view, partially in cross-section taken along lines 11—11 as shown in FIG. 10 and shown with the medication cartridge in the dental syringe and with the needle shield in the retracted position;

FIG. 12 is a fragmentary side cross-sectional view also taken along lines 11—11 as shown in FIG. 10 and shown with the needle shield in the extended position;

FIG. 13 is an enlarged scale, fragmentary side sectional view taken along lines 13—13 as shown in FIG. 11 and showing details of the collar and needle shield thereof;

FIG. 16 is an enlarged scale, perspective view of the collar shown in FIG. 11.

DETAILED DESCRIPTION OF THE PREFERRED EMBODIMENTS

In the preferred embodiment, the invention is intended to be used in conjunction with a standard hypodermic syringe; however, a protective needle shield in accordance with the invention may be modified for use with any medical, laboratory or dental device having a needle, such as a blood collection tube holder or dental syringe with a double ended needle (as described hereinafter) without departing from the contemplated scope of the present invention. Accordingly, as used herein, the term "syringe" is intended to include any medical or scientific device including a needle wherein it is desired to protect a user from accidental needle sticks.

In describing the invention, the "distal end" of a part refers to the end of the part closest to the needle point. The "proximal end" of a part refers to the end furthest from the needle point.

Figure 8:
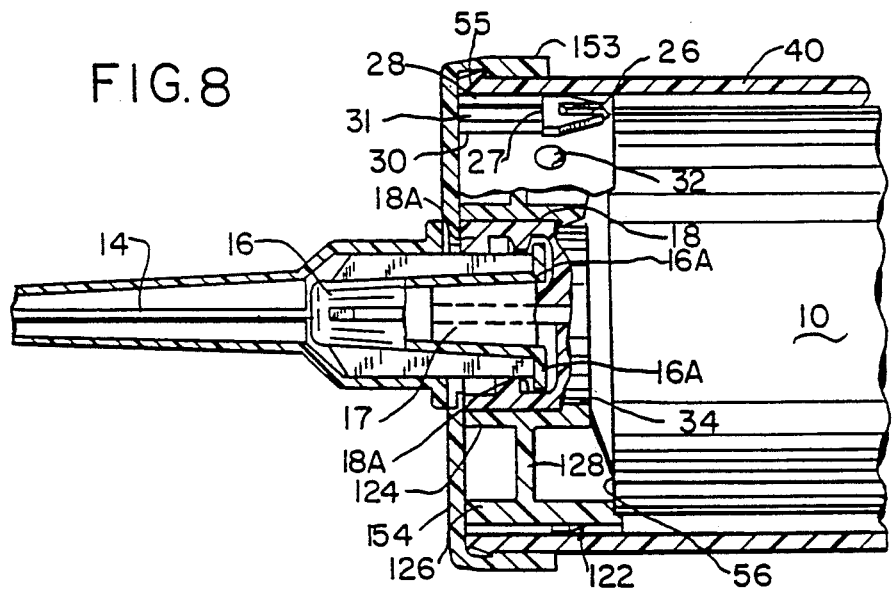
FIG. 8 is a side sectional view showing a collar construction for use with a large diameter barrel.

FIGS. 1-6 show a conventional syringe comprising a tubular barrel 10 having a finger flange 11, a plunger 12 slidable within the barrel 10, and a needle assembly through which the contents of the barrel are dispensed when the plunger 12 is depressed. The barrel 10 may be tapered very slightly (not shown) from a larger diameter proximal end to a smaller diameter distal end for molding purposes. The needle assembly comprises a needle 14 and a hub 16 at the proximal end of the needle. As is standard, a conically shaped luer tip 17 and luer lock skirt 18 are integrally formed at the distal end of barrel 10 with the luer lock skirt 18 encircling the luer tip 17. As shown in FIG. 8 (directed to a different collar construction and described in detail below), the interior surface of the luer lock skirt 18 includes an internal thread 18A adapted to threadably engage complementary locking ears 16A on the needle hub 16. The exterior surface of the luer lock skirt 18 includes a multiplicity of ribs 19 parallel to the central axis of the barrel.

A needle sheath 20 covers the needle 14 as a protective device. The sheath 20 frictionally engages the hub 16 and can be used to disconnect the needle assembly from the luer lock skirt 18 in conventional fashion.

The collar employed in accordance with the preferred embodiment of the invention is shown generally at 22 (FIGS. 2, 6 and 8). As mentioned above, although collar 22 is shown as a separate piece, it is anticipated that the collar (or its functional equivalent) may be integrally formed as a part of the barrel 10 without substantial modification of the present invention. In this embodiment, the collar 22 includes six equally spaced and integrally formed identical triangular protrusions 24, with the apex of each protrusion extending away from the needle. A plurality of keyways 25 are formed on the collar 22 between each adjacent pair of protrusions 24.

Each triangular protrusion 24 includes angled surfaces 24A and 24B, side surfaces 25C, a slot 26 and a surface 27 which is generally circumferential and functions as a stop for the keys 42 as further explained below. The slot 26 includes a sloped distal surface 26A. It is not absolutely necessary that protrusions 24 be triangular in shape and it is anticipated that other configurations may be used to guide the keys 42 into the keyways 25 during the assembly process as described below. The slot 26 is formed in protrusion 24 and extends proximally to the point of the protrusion 24 to expose the detenting surface 26A and facilitate the entry of the detent 50 into the slot 26 during assembly. At the forward end of each protrusion 24, two walls 28 and 30 extend toward the needle 14. A rectangular locking slot 31 is formed between each pair of walls 28 and 30. The walls, 28 and 30, are preferably ramp shaped in cross section as shown in FIGS. 4, 5 and 6. As is shown in FIGS. 3, 4, 5 and 6, the surface of locking slot 31 is slightly elevated relative to the level of the keyways 25, i.e., the barrel diameter at the locking slots 31 is slightly greater than the barrel diameter at the keyways.

The slight increase in the collar diameter at the locking slots 31 removes some of the slack between the needle shield 40 (described below) and the collar 22 resulting from the slight taper of the barrel 10 in the preferred embodiment. This prevents or at least minimizes wobble or play of the needle shield 40 when it is locked in the extended position. A spherical detent 32 is positioned between each pair of triangular protrusions 24 with the distal edge of the spherical detents 32 located distally of the bases of triangular projections 24.

As shown most clearly in FIG. 3, the proximal end of collar 22 includes a peripheral rigid internal tooth 34 adapted to engage the ribs 19 in the luer lock skirt 18 and retain the collar 22 on the syringe. The collar 22 is molded of a rigid plastic material such as polycarbonate resin so that when the collar 22 is pushed over the luer lock skirt 18, the angled surface of the tooth 34 allows the tooth 34 to move over the ribs 19 until the proximal end of the collar 22 is seated adjacent the distal end of the barrel so that the tooth 34 deforms the ribs 19 of the luer lock skirt 18 to permanently retain the collar in place on the syringe barrel 10. As an alternative, a circumferential groove may be formed in the outer surface of the luer lock skirt 18 to receive the tooth 34 of the collar 22 therein. This is unnecessary in the preferred embodiment in which the yieldable ribs 19 cold flow into the configuration shown in FIG. 3 but may be desirable in the case of syringes which do not include ribs molded on the exterior surface of the luer lock skirt. Instead of mechanically interlocking the collar 22 and barrel 10, other fastening means such as ultrasonic welding or adhesives may be used within the scope of the invention. The diameter of collar 22 as measured in the area of the keyways 25 is greater than the outer diameter of the syringe barrel 10 adjacent to the collar.

Figure 7:
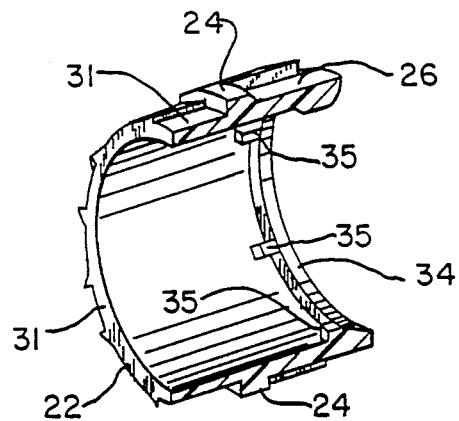

The rigid peripheral tooth 34 will bite sufficiently into the outer surface of the luer skirt 18 to prevent axial movement of collar 22 but in some cases slight rotation or rocking of the collar 22 may occur. To prevent this, the tooth 34 may be formed with gaps (not shown) so that not all of the ribs 19 on the outside of the luer lock skirt 18 will be deformed. The nondeformed ribs 19 will fall into the gaps in the modified tooth and resist rotation or rocking of the collar 22 relative to the barrel 10. Alternatively, as shown in FIGS. 7 and 8, the inner surface of the collar 22 may be provided with lugs 35 molded on the inside of the collar 22 and adapted to fit between the ribs 19 on the outside of the luer lock skirt 18 to prevent rotational movement of the collar 22 with the meshed ribs 19.

The needle shield 40 comprises an elongated plastic cylinder (e.g., made of polypropylene) having three keys 42 integrally formed on its interior surface. An end rim 44 is formed at the proximal end of the needle shield 40. As shown in FIG. 2, the end rim 44 is adapted to abut against the proximal end of the collar 22 to limit the forward movement of the shield. Each of the keys 42 includes a distal triangular point 46 which is designed to extend from the distal end of the needle shield 40 to a location just short of the distal point of the triangular protrusions 24 on collar 22 when the needle shield 40 is in the extended position (FIG. 2). The end rim 44 includes three cutout sections 45 which align with each of the keys 42. The cutout sections 45 facilitate the process for molding keys 42 but serve no functional purpose during the operation of the present embodiment. At their proximal ends, the keys 42 terminate in flat end surfaces 48. With the three keys 42 in the keyways 25 in the retracted position (FIG. 1), rotational movement of the needle shield 40 is prevented by contact between the edges of keys 42 against the side surfaces 24C of the protrusions 24; therefore, torque can be applied to the needle of this embodiment while manually holding the needle shield 40 to thread (or unthread) needles onto (or from) the syringe. This cannot be done with constructions in which a needle shield rotates freely with respect to the syringe.

Three detents 50 are also formed on the inner distal surface of the needle shield 40. These detents 50 may be equally spaced and are adapted to be received within the slots 26 in the triangular protrusions 24 to releasably retain the needle shield 40 in its retracted position (FIG. 1). In the preferred embodiment, the detents 50 are preferably spaced approximately thirty degrees from an adjacent key 42. Each of the detents includes a sloped distal surface 50A and a proximal surface 50B more gradually sloped than distal surface 50A.

In the retracted position, the distal end of needle shield 40 terminates at the same point as the distal end of collar 22. An end cap 52 (see FIG. 2) is placed on the distal end of the needle shield 40. The end cap 52 is molded from a resilient plastic material (such as polyallomer) and includes a side wall 53 and an end wall 54 which are adapted to be positioned between the distal end of collar 22 and the proximal end of the needle sheath 20 (FIG. 1) for substantially closing the distal end of the needle shield 40. The side wall 53 is shaped as shown in FIG. 1 so that the end cap 52 may be retained on the needle shield 40 by the interlocking mechanical engagement of the side wall 53 and a complementary projection 55 at the forward end of the needle shield 40. The end cap 52 need not be a separate part and may be formed as an integral part of needle shield 40.

The end wall 54 includes a central needle aperture which is made small enough that the end of needle shield 40 is closed to the maximum extent while allowing the locking ears 16A of needle hub 16 to be inserted through the aperture to permit needles to be mounted and removed while the needle shield 40 is in its retracted position (FIG. 8). The aperture is not, however, large enough to allow the proximal end of the needle sheath 20 to pass through it. The use of the smaller sized needle aperture reduces the likelihood that a child or person with small fingers may accidentally contact the needle point. The end cap 52 also makes the distal end of needle shield 40 more rigid and resistant to deformation when dropped or otherwise impacted upon a hard surface.

Additionally, the rim 54 and its position between the proximal end of needle sheath 20 and the distal end of barrel 10 serves a functional purpose when removing or installing needles on the luer tip 17 (FIG. 8), for example, in a situation where the filling and injection needles are different. When a needle is to be mounted on a syringe, the syringe is held by the needle shield 40 with the needle shield 40 in its retracted position. The needle hub 16 which projects from the proximal end of the needle sheath 20, is inserted through the aperture in the end wall 54 and the needle hub 16 is telescoped onto the luer tip 17. Using the conventional cooperative wrenching tabs (not numbered) of the needle sheath 20 and needle 14, the needle hub 16 is rotated by twisting and pushing with the sheath to thread the locking tabs 16A within the internal threads 18A in the luer skirt 18 until needle 14 is mounted on the syringe. As the needle hub 16 is threaded onto the luer tip 17, the needle 14 moves axially relative to the needle sheath 20. The needle shield 40 is prevented from rotating by the contact of the keys 42 against surfaces 24C of the protrusions 24, while the rim 54 provides a surface against which the needle sheath 20 can be forced. Without this feature, the user could not grasp the needle shield 40 alone when installing and removing the needle 14 since the force exerted by the needle hub 16 on the luer tip 17 of the syringe would push the syringe out of the needle shield 40. This would mean that the user would have to remember to grasp the barrel 10 and not the needle shield 40 when removing and attaching the needle 14.

Figure 9:
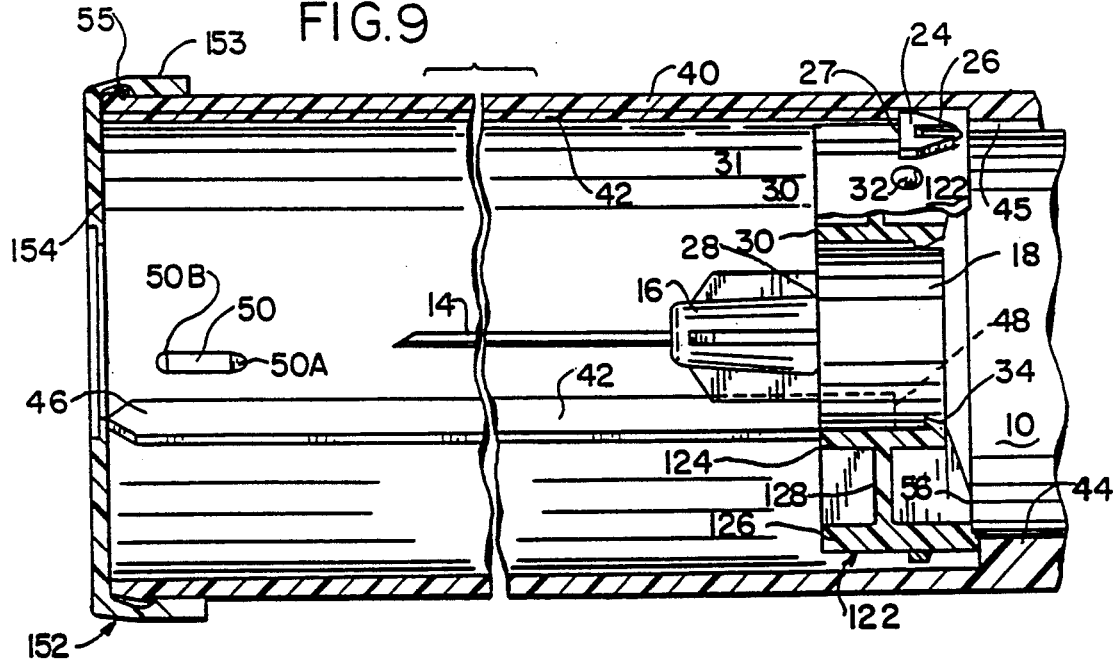
FIG. 9 is an enlarged side sectional view showing a needle shield in its extended position relative to the collar of FIG. 8.

The end wall 54 is particularly important when the invention is used in conjunction with large diameter barrels. The preferred type of construction for the larger diameter syringe barrels is shown in FIGS. 8 and 9 wherein like numerals are used to identify parts identical to those shown in the embodiment of FIGS. 1-6. In FIGS. 8 and 9 the needle 14 and hub 16 are the same as in FIG. 1 as is the luer tip 17 and the luer lock skirt 18. In this embodiment, however, the collar 122 includes two concentric hubs or sleeves 124 and 126 which are supported by an annular strut 128 to preferably form an I-beam shaped structure in cross-section as shown in FIG. 9. The cross-sectional shape is not critical, however, and those skilled in the art will readily understand that the cross-section could be cup or channel-shaped, with a web extending either distally or proximally between the concentric hubs or sleeves. The end cap 152 includes a side wall 153 and an end wall 154 which cover a substantial portion of the barrel opening and thus greatly reduce the risk of accidental needle stick injury when the shield is in its extended position.

The device of the preferred embodiment is preferably assembled as follows. The needle shield 40 is inserted on the distal end of the barrel 10 of an assembled syringe and moved to the retracted position as shown in FIG. 1. With the shield 40 held in the retracted position, the collar 22 is then placed over the luer lock skirt 18 and inside the needle shield 40. As the triangular protrusions 24 on collar 22 contact the triangular points 46 at the end of keys 42 on the needle shield 40, the collar 22 is pushed onto the luer lock skirt 18, which causes the needle shield 40 to rotate until the keys 42 are positioned in the keyways and slide over the spherical detents 32 located between the adjacent triangular protrusions 24. The collar 22 is pushed inwardly until the proximal end of the collar butts up against the distal face 36 of the syringe barrel 10. In this position, as shown in FIG. 3, the three detents 50 are seated in the slots 26 of three of the protrusions 24. After the needle shield 40 and collar 22 have been assembled on the syringe, the end cap 52 is placed on the needle shield 40. Finally, the needle 14 with its needle sheath 20 may then be attached to the luer tip 17 to complete the assembly.

Alternatively, the collar 22 may initially be positioned within the shield 40 so that the keys 42 positioned in the appropriate keyways 25. The needle shield 40 and collar 22 may then be telescoped together over the syringe barrel 10 with the collar 22 being forced onto the luer lock skirt 18 as the needle shield 40 is moved to the retracted position wherein the proximal end of the collar 22 contacts the distal face of the syringe barrel. This procedure, with appropriate tooling, may be used with the end cap 52 in place on the needle shield 40 to allow this assembly process to be used with a needle shield 40 having an end wall 54 integrally formed as a portion of the needle shield 40 as mentioned above. Additionally, it is anticipated that this alternative assembly method may be used with an open needle shield 40 wherein the end cap 52 may be placed on the needle shield 40 after assembly.

The syringe of the present invention may be used in a conventional manner. The needle sheath 20 is removed from the needle 14 and the medication is drawn into barrel 10 by withdrawing the plunger 12 as the needle shield 40 is in the retracted position. After the contents of the syringe have been injected into the patient, the needle shield 40 is pushed distally into the extended position shown in FIG. 2. As this occurs, the keys 42 slide in the keyways 25 over the spherical detents 32 located between the adjacent protrusions 24 on collar 22 (FIG. 4) and the distal surfaces 50A of the detents 50 on the needle shield 40 will slide over the surfaces 26A on slots 26 (FIG. 2). The user can feel a slight click as the end surfaces 48 of the keys 42 clear the spherical detents 32, which signals the user that the needle shield 40 is fully extended.

To lock the needle shield 40 in the extended position, the user then rotates the needle shield 40 to cause the keys 42 to move over the adjacent ramps 28 (or 30) until the keys 42 fall into the locking slots 31 formed between each pair of ramps 28 and 30 (see FIG. 5). Because of the arrangement of the ramps 28 and 30, the needle shield 40 may be locked by rotating it either clockwise or counterclockwise. When the keys 42 are positioned in the locking slots 31, the proximal end surface 48 of each key 42 abuts against the squared off surface 27 of one of the triangular protrusions 24 so that the needle shield cannot be returned to its retracted position without application of excessive force. Because of the interlocking relationship of the square key 42 and the locking slots 31, the needle shield 40 can no longer be rotated and, accordingly, the needle shield 40 is locked in the extended position.

In certain situations, it may be desirable to extend the needle shield 40 to the extended position shown in FIG. 2 without locking the needle shield 40 in place. For example, if a syringe is to be filled at a location remote from the patient, rather than replacing the needle sheath 20 on the needle 14 after the syringe is filled, it is preferable to extend the needle shield 40 so that it functions as a temporary protective element while the syringe is carried to the patient. Use of the needle shield 40 in this fashion is facilitated by the spherical detents 32 on the collar 22. These spherical detents 32 are positioned in each of the keyways 25 between the triangular protrusions 24 so that when the needle shield 40 is pulled to the extended position (FIG. 2), the flat end surface 48 of each of the keys 42 abut against one of the detents 32. This prevents the needle shield 40, when it is in the extended position, from being retracted unless sufficient force is applied to move the keys 42 over the spherical detents 32. Hence, in this situation, the needle shield 40 is first extended as a temporary shield for the needle 14 and then returned to the retracted position for the patient's injection. Once the injection has been administered, the needle shield 40 may again be extended and then locked by rotation so that the needle shield 40 cannot be retracted. If it is desired to return the needle shield 40 to its retracted position rather than locking the needle shield 40 in its extended position, the gradual slope of surface 50B of the detent 50 allows the detent to be pushed over the squared off surface 27 prior to returning the needle shield 40 to its fully retracted position.

A further embodiment of the present invention is illustrated in FIGS. 10 through 16 with the collar 22 and needle shield 40 of the preferred embodiment adapted for use on a conventional dental syringe of the type adapted to receive a medication cartridge removably mounted therein. The dental syringe of the present embodiment is generally designated as dental syringe 150.

As illustrated in FIGS. 10 and 11, the dental syringe 150 of the present embodiment includes an elongate and tubular cartridge holder assembly 166 adapted to receive a conventional medication cartridge 167 therein. A conventional injector assembly 152 is mounted on the proximal end of the cartridge holder assembly 166. The distal end of the cartridge holder assembly 166 includes a double ended needle assembly 176 mounted therein and a tubular collar assembly 186 mounted thereon. The collar assembly 186 slidably contacts an elongate and tubular needle shield assembly 210 which is longitudinally movable over the cartridge holder assembly 166 and the collar assembly 186. A conventional needle sheath assembly 220 removably mounted on the distal end of the needle shield assembly 210 thereon.

As illustrated in FIG. 11, the cartridge holder assembly 166 of the present embodiment includes an elongate and tubular proximal barrel section 168, a tapered barrel section 170 fixedly mounted on the distal end thereof and an integral distal barrel section 172 on the distal end of the tapered barrel section 170. The proximal end of the proximal barrel section 168 includes a pair of radially extending retention flanges 169, the function of which are described hereinafter. The interior surface of the proximal barrel section 168 has a generally uniform internal diameter which is adapted to receive a conventional medication cartridge 167 therein.

As illustrated in FIG. 11, the medication cartridge 167 referred to herein is a commercially available medication cartridge having an injectable medication therein, one example of which is a 1.8 ml cartridge which contains a 2% lidocaine HCl injection with epinephrine in a concentration of 1:100,000 manufactured by Astra Corporation of Worchester, Massachusetts, U.S.A. The medication cartridge 167 includes an elongate glass cylinder 165 with a rubber piston or plunger member 171 movably mounted in the proximal end of the cylinder 165. The distal end of the medication cartridge 167 includes a metal cap 173 fixedly mounted on a reduced portion of the cylinder 165. The metal cap 173 includes a central orifice (not shown) positioned over a needle pierceable diaphragm 175.

As further illustrated in FIG. 11, the tapered barrel section 170 at the distal end of the cartridge holder assembly 166, decreases in external diameter from the distal end of the proximal barrel section 168 to a smaller diameter and integrally connected, cylindrically-shaped distal barrel section 172. The external surface of the distal barrel section 172 preferably includes four equally spaced ribs 184 thereon (FIG. 12). The distal end of the ribs 184 extend from the distal end of the distal barrel section 172 so that the outer diameter of the distal barrel section 172 is generally uniform about and along the longitudinal axis thereof.

The barrel section 172 surrounds the needle hub 174 of the integral double ended needle assembly 176 as illustrated in FIG. 11. The needle assembly 176 further includes an elongate and hollow distal needle section 178 which extends beyond the distal end of the cartridge holder assembly 166 to a sharpened distal needle point 179 and an integral and elongate hollow proximal needle section 180 which extends into and within the distal end of the cartridge holder assembly 166 to a sharpened proximal needle point 181 located proximally of the tapered barrel section 170. A cylindrical cartridge positioning hub 182 is located on the proximal side of the needle hub 174 and extends proximally from the needle hub 174 to a location generally adjacent to the midpoint of the tapered barrel section 170. The positioning hub 182 encircles and supports the majority of the proximal needle section 180 and is adapted to contact the distal end of the medication cartridge 167 when the medication cartridge 167 is inserted into the cartridge holder assembly 166 as described hereinafter.

As illustrated in FIGS. 12 and 16, the tubular collar assembly 186 of the present embodiment preferably includes six equally spaced and integrally formed triangularly-shaped protrusions 188 which extend radially from the circumferential surface of the collar assembly 186. The apex of each of the triangularly-shaped protrusions 188 is positioned along the proximal side of the collar assembly 186 to assist in the assembly of the present embodiment as described hereinafter. Each of the protrusions 188 also include angled surfaces 188A and 188B, side surfaces 192, and a distal surface 196 which extend perpendicularly from the surface of the collar assembly 186. A recessed slot 194 extends distally from the apex of each of the triangularly-shaped protrusions 188 to a sloped distal surface 194A, the function of which is described hereinafter. The distal surface 196 of each protrusion 188 forms a generally circumferential surface along the distal side of the protrusion 188 approximately midway along the external surface of the collar assembly 186. The side surfaces 192 of each adjacent pair of protrusions 188 form keyways 190 therebetween, the function of which is described hereinafter. A radially extending and spherical detent 208 is positioned in the keyways 190 between each pair of protrusions 188 such that the distal edge of each spherical detent 208 is located slightly distal to the distal surface 196 of each protrusion 188 and the proximal edge of each spherical detent 208 is located slightly proximal to the side surfaces 192 of each protrusion 188.

Figure 14:
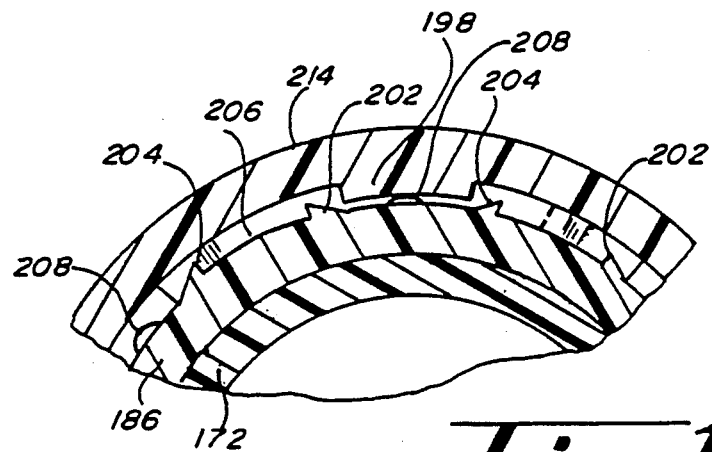
FIG. 14 is a fragmentary sectional view taken along lines 14—14 in FIG. 11 and showing a portion of the needle shield in the extended position prior to rotation of the needle shield.
Figure 15:
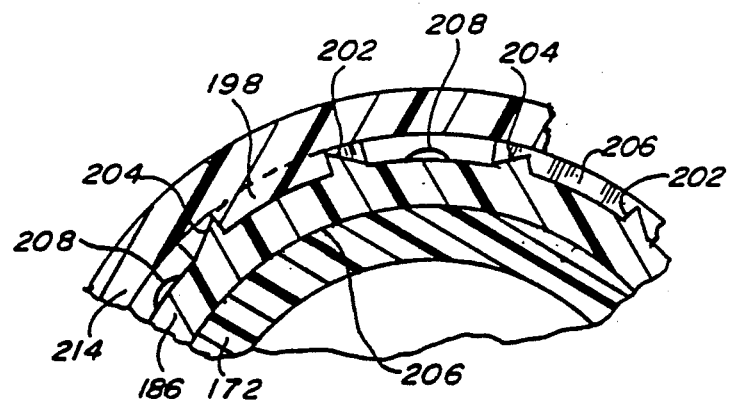
FIG. 15 is a fragmentary sectional view taken along lines 14—14 in FIG. 11 and showing a portion of the needle shield in the extended and locked position after rotation.

As illustrated in FIGS. 14 and 15, a pair of parallel walls, 202 and 204, are positioned radially along the lengthwise dimension of the collar assembly 186 adjacent to the distal surface 196 of each protrusion 188. The walls, 202 and 204, form a rectangularly shaped locking slot 206 therebetween, the function of which is described hereinafter. The walls, 202 and 204, preferably include a ramp shaped wall surface on the external side thereof and a perpendicular wall surface on the internal side thereof. The surface of the locking slot 206 is slightly elevated relative to the level of the keyways 190, i.e., the collar diameter at the locking slots 206 is slightly greater than the collar diameter at the keyways 190. This slight increase in collar diameter at the locking slots. 206 removes some of the slack or wobble which may occur between the needle shield assembly 210 (described hereinafter) and the collar assembly 186 to decrease the likelihood that the needle shield assembly 210 will wobble or move relative to the cartridge holder assembly 166 when the needle shield assembly 210 is moved to a locked and extended position (FIG. 12) described hereinafter.

As illustrated in FIG. 13, the internal surface of the collar assembly 186 includes a wedge-shaped internal tooth member 212 adjacent to the proximal end of the collar assembly 186 which is adapted to engage the outer surface of the distal barrel section 172 and retain the collar assembly 186 on the distal barrel section 172 of the cartridge holder assembly 166 during assembly of the present embodiment as described hereinafter. The collar assembly 186 of the present embodiment is molded of a rigid plastic material such as a polycarbonate resin so that the collar assembly 186 causes a slight deformation of the ribs 184 and distal barrel section 172 as the collar assembly 186 placed on the distal barrel section 172 of the cartridge holder assembly 166. Alternately, raised yieldable ribs (not shown) may be formed on the distal barrel section 172 or gaps may be formed in the tooth member 212 on the collar to function in the same manner as described above with respect to the preferred embodiment. Additionally, other means of interlocking the collar 186 to the distal barrel section 172 such as ultrasonic welding or adhesives are contemplated and may be used without departing from the scope of the present invention.

With reference to FIGS. 10 and 11 of the drawings and as heretofore described, the cartridge holder assembly 166 of the present embodiment includes a conventional injector assembly 152 mounted on the proximal end thereof. The injector assembly includes a bore 153 therethrough for slidably receiving an elongate plunger rod 154 therein. The plunger rod 154 is provided with a conventional enlarged and circular finger ring 156 at the proximal end thereof and a triangularly-shaped and sharpened barb member 158 extending from the distal end thereof. The injector assembly 152 further includes a generally cylindrical body section 151 having a proximally positioned enlarged oval-shaped finger flange 160 which is adapted to be grasped by the fingers of the user. A cylindrical locking ring 162 is slidably positioned on the body section 151 of the injector assembly 152 distal to the finger flange 160. The body section 151 also includes a generally cylindrically-shaped and resilient, body member 164 which extends distally from the finger flange 160. The body member 164 includes an integral and frustoconically-shaped distal portion 161 having a retaining lip or rim 164A thereon. A pair of longitudinally extending slots or channels 165 are provided on opposite lateral sides of the body member 164. Each channel 165 includes a triangularly-shaped recess 163 adjacent to the distal end thereof which is adapted to receive one of the retention flanges 169 from the cartridge holder assembly 166 therein, as will be discussed more fully hereinafter.

As illustrated in FIGS. 12 and 13, the needle shield assembly 210 of the present embodiment preferably includes an elongate and tubular proximal shield section 214 having three equally spaced and rectangularly-shaped elongate keys 198 integrally formed along the interior surface thereof and a tapered shield section 216 which decreases in external diameter from the distal end of the proximal shield section 214 to an integral distal shield section 218. The keys 198 preferably extend lengthwise between the distal and proximal ends of the proximal shield section 214 and include triangularly-shaped distal ends and flat-proximal ends, the function of which are described hereinafter. An end rim 222 is formed along the inner surface of the proximal end of the proximal shield section 214 and is adapted to extend radially inwardly therefrom. Three equally spaced and inwardly extending oblong-shaped detents 200 are formed along the internal surface of the distal end of the needle shield assembly 210. These detents 200 are preferably spaced approximately thirty degrees from an adjacent key 198 and include sloped distal surfaces, the function of which are described hereinafter.

The distal shield section 218 of the needle shield assembly 210 is a cylindrically shaped tubular member having a centrally located needle aperture 211 therein, as illustrated in FIGS. 11 and 12. The needle aperture 211 of the distal shield section 218 is sized to allow the distal needle section 178 and the needle hub 174 of the needle assembly 176 to pass therethrough. The tapered shield section 216 and the reduced diameter distal shield section 218 allow the dentist to observe the entire distal needle section 178 of the needle assembly 176 during a dental procedure and does not interfere with any other instruments which may be simultaneously present in the patient's mouth. Additionally, the use of the tapered shield section 216 and the smaller sized needle aperture 211 reduces the likelihood that a child or person with small fingers may accidentally contact the distal needle point 179 when the needle shield assembly 210 is in the extended position as described hereinafter.

As briefly described above, the needle sheath assembly 220 is adapted to be removably attached to the distal shield section 218 of the needle shield assembly 210. As illustrated in FIGS. 10 and 11, the needle sheath assembly 220 includes an elongate and tubular body section 221 which is adapted to protect the distal needle section 178 and distal needle point 179 of the needle assembly 176 prior to use of the present embodiment. The proximal end of the needle sheath assembly 220 includes an enlarged rim member 223. The proximal end of the needle sheath assembly is adapted to be attached to the distal section 218 of the needle shield assembly 210 by frictional contact, adhesives or heat staking therebetween.

Assembly of the dental syringe 150 is relatively simple and may be automated. Initially, the collar assembly 186 is positioned within the proximal shield section 214 of the needle shield assembly 210 by inserting the collar assembly 186 through the distal end of the proximal shield section 214 so that the triangularly-shaped distal ends of the keys 198 are position between the triangularly-shaped protrusions 188 and in the appropriate keyways 190 on the collar assembly 186. The tapered shield section 216 and integral distal shield section 218 are then placed on the distal end of the proximal shield section 214 so that the tapered shield section 216 is retained on the distal end of the proximal shield section 214. This may be accomplished by ultrasonic welding, adhesives or interlocking mechanical engagement of a grooved sidewall 226 with a complementary distally extending projection 228 located at the distal end of the proximal shield section 214 as illustrated in FIG. 11. The needle shield assembly 210 and collar assembly 186 are then telescoped over the distal end of the cartridge holder assembly 166 so that the tooth member 212 of the collar assembly 186 is forced over the distal barrel section 172 by the needle shield assembly 210 until the proximal end of the collar assembly 186 is engaged on the distal barrel section 172 in a predetermined location.

In the present embodiment, the rim member 223 of the needle sheath assembly 220 is then attached to the distal shield section 218 of the needle shield assembly 210. Alternately, if the needle assembly 176 is separate from the distal barrel section 172, the needle hub 174 of the needle assembly 176 is attached to the distal barrel section 172, as described above, and then the needle sheath assembly 220 is attached to the distal shield section 218. It is also contemplated that the other assembly methods described above with respect to the preferred embodiment are readily adaptable for the assembly of the dental syringe 150 of the present embodiment.

The dental syringe 150 of the present embodiment may be used in a conventional manner to perform various dental procedures. Initially, the user will insert a medication cartridge 167 into the proximal end of the cartridge holder assembly 166. The plunger rod 154 of the injector assembly 152 is then moved proximally to a retracted position and the injector assembly 152 is attached to the cartridge holder assembly 166 by inserting the retention flanges 169 of the cartridge holder assembly 166 into the recesses 163 located in channels 165 of the injector assembly 152. The user may then lock the injector assembly 152 on the proximal end of the cartridge holder assembly 166 by moving the locking ring 162 distally along the body member 164 to compress the frustoconically-shaped distal portion 161 of the body member 164 to retain the retention flanges 169 of the cartridge holder assembly 166 within the recesses 163 in the channels 165 of the body member 164. The user may then grasp the finger ring 156 on the injector assembly 152 and move the plunger rod 154 distally until the barb member 158 pierces and is seated in the plunger member 171 on proximal end of the medication cartridge 167 and the proximal needle point 181 pierces the diaphragm 175 through the orifice in the metal cap 173 on the distal end of the medication cartridge 167.

As illustrated in FIG. 11, the medication cartridge 167 is loaded in the cartridge holder assembly 166 and the needle shield assembly 210 is in the retracted position.

In the retracted position, the needle shield assembly 210 is positioned about the cartridge holder assembly 166 so that the proximal end of the proximal shield section 214 is adjacent to the lip 164A of the body member 164 on the injector assembly 152; the needle aperture 211 on of the distal shield section 218 is adjacent to the needle hub 174 of the needle assembly 176 and the needle sheath assembly 220 encloses the distal needle section 178 and distal needle point 179 of the needle assembly 176. In the retracted position, the triangularly-shaped distal ends of the keys 198 are positioned in the keyways 190 between the side surfaces 192 of the protrusions 188 and in contact with the proximal edge of the spherical detents 208 on the collar assembly 186. Additionally, the detents 200 on the needle shield 210 are aligned within the slots 194 on the protrusions 188 so that the proximal surface of the detents 200 will contact the sloped distal surface 194A of the slots 194 to releasably retain the needle shield assembly 210 in the retracted position.

In order to administer an injection, the needle sheath assembly 220 is initially removed from the distal shield section 218 to expose the distal needle point 179 of the needle assembly 176. The user may then administer the injection in a conventional manner by inserting the distal needle point 179 into the injection site while grasping the finger flange 160 and moving the finger ring 156 on the plunger rod 154 distally with respect to the finger flange 160. The distal movement of the plunger rod 154 causes the barb member 158 to move the plunger member 171 distally in the cylinder 165 of the medication cartridge 167 to dispense the medication through the distal needle point 179 on the needle assembly 176 and into the injection site.

Once the contents of the dental syringe 150 have been injected into the patient, the needle shield assembly 210 is pushed distally to the extended position as shown in FIGS. 10 and 12. As the needle shield assembly 210 is moved to the extended position, the keys 198 will slide longitudinally in the keyways 190 over the spherical detents 208 on the collar assembly 186 and the angled distal surfaces on the detents 200 on the needle shield assembly 210 will slide over the angled detenting surfaces 194A on slots 194 to release the needle shield assembly 210 from the retracted position. As the needle shield assembly 210 reaches the extended position, the spherical detents 208 on the collar 186 will signal the user that the needle shield assembly 210 has reached the fully extended position by releasing from the flat proximal ends of the keys 198, once the keys 198 pass beyond the spherical detents 208. Additionally, as illustrated in FIG. 12, when the needle shield assembly 210 reaches the extended position, the end rim 222 on the proximal end of the needle shield assembly 210 will contact the proximal end of the collar assembly 186 to prevent further distal movement of the needle shield assembly 210 along the cartridge holder assembly 166 and the collar assembly 186.

As generally illustrated in FIGS. 12 and 14, when the needle shield assembly 210 is in the extended position, the tapered shield section 216 and the distal shield section 218 of the needle shield assembly 210 extend beyond the distal needle point 179 of the needle assembly 176 and the end rim 222 on the proximal end of the proximal shield section 214 contacts the proximal end of the collar assembly 186. In this extended position, the proximal end of the keys 198 are positioned adjacent to the proximal side of the keyways 190 and the flat-proximal ends of the keys 198 are located along the distal edge of the spherical detents 208 and adjacent to the walls, 202 and 204 and locking slots 206.

If the user desires to lock the needle shield assembly 210 in a locked and extended position (FIG. 12) rather than the releasable extended position described above, the user may rotate the needle shield assembly 210 clockwise or counterclockwise about the cartridge holder assembly 166 and the collar assembly 186. Rotation of the needle shield assembly 210 will cause the keys 198 on the needle shield assembly 210 to move over the ramp shaped surface of the adjacent walls, 202 or 204, on the collar assembly 186 until the keys 198 fall into the locking slots 206 formed therebetween. When the keys 198 are positioned in the locking slots 206, the flat-proximal end of each key 198 abuts against the distal surface 196 of one of the protrusions 188 so that the shield cannot be moved proximally and returned to the retracted position. Because of the interlocking relationship between the sides of the keys 198 and the perpendicular side surfaces of the walls, 202 and 204, the needle shield assembly 210 can no longer be rotated and, accordingly, the needle shield assembly 210 is in a locked and extended position (FIG. 15).

In certain situations, it may be desirable to move the needle shield assembly 210 to the extended position (FIG. 14) without having the needle shield assembly 210 in a locked and extended position (FIG. 15). For example, if a dental syringe 150 is preloaded with the medication cartridge 167 at a location remote from the patient; stored on a dental tray prior to use or if the user desires to verify that the medication cartridge 167 is properly seated in the cartridge holder assembly 166, it may be preferable to extend the needle shield assembly 210 beyond the distal needle point 179 so that the needle shield assembly 210 functions as a temporary protective element prior to the actual use of the dental syringe 150. Use of the dental syringe 150 in this manner is facilitated by the spherical detents 208 on the collar assembly 186. As described above, these spherical detents 208 are located in each of the keyways 190 between the protrusions 188 so that when the needle shield assembly 210 is pushed to the extended position, the flat-proximal end of each of the keys 198 will release from the spherical detents 208 and the end rim 222 of the needle shield assembly 210 will contact the proximal end of the collar 186. The spherical detents 208 prevent the needle shield assembly 210 from being accidentally or inadvertently retracted unless sufficient proximal force is applied to the needle shield assembly 210 to move the keys 198 proximally over the spherical detents 208. Once the injection has been administered, the needle shield assembly 210 may be moved distally to the extended position and then rotated so that the keys 198 fall into the locking slots 206 to lock the needle shield assembly 210 in the locked and extended position as described above.

In this light, it should be appreciated that the present invention provides a safety dental syringe which allows a medication cartridge to be inserted into the dental syringe through the proximal end thereof. Additionally, the reduced diameter distal end of the present invention allows the user to observe the distal end of the needle during a dental procedure and does not interfere with any other instruments which may be present in the patient's mouth. The relatively small size of the needle aperture in the distal end of the needle shield also prevents accidental contact with the distal needle point when the needle shield is in the extended position. Finally, the cylindrical shape of the distal end of the needle shield allows the user to move the needle shield to the extended position to verify that the medication cartridge is properly seated in the cartridge holder without removing the needle sheath.

It should be further understood that the above described embodiments may be modified in certain aspects for use on nearly any medical, or laboratory syringe. Therefore, the foregoing is intended to be descriptive of the preferred form of the embodiments described above while the scope of the present invention is intended to be defined by the following claims.

What is claimed is:

1. A medication containing syringe comprising:
   a first tubular member having distal and proximal ends and adapted to receive a medication cartridge therein,
   a plunger rod assembly including a reciprocally mounted plunger rod mounted adjacent said proximal end of said first tubular member and adapted to contact a portion of the medication cartridge;
   a double ended hollow needle assembly including a needle hub thereon, said needle hub being operatively mounted on said distal end of said first tubular member, said needle assembly having a needle point on the distal and proximal ends thereof whereby said proximal needle point of said needle assembly is adapted to pierce the medication cartridge for fluid communication with the medication contained therein and said distal needle point of said needle assembly extends distally beyond said distal end of said first tubular member;
   collar means operatively associated with said first tubular member, said collar means including recessed keyway thereon; and
   a second tubular member positioned about said first tubular member and said collar means, said second tubular member having distal and proximal ends and an inwardly directed and elongate key thereon and wherein the length of said key is greater than the length of said keyway and said key slidably contacts said collar means, said second tubular member being longitudinally movable over said first tubular member and said collar means between a retracted position wherein said distal needle point is exposed and an extended position wherein said distal needle point is protected.

2. The medication containing syringe of claim 1, wherein locking means are provided between said second tubular member and said collar means and said second tubular member is rotatably movable from said extended position to a locked and extended position wherein said second tubular member is prevented from being returned to said retracted position.

3. The medication containing syringe of claim 2, wherein said second tubular member includes said key thereon to facilitate the coaxial movement of said second tubular member along said collar means and said first tubular member between said retracted and extended positions.

4. The medication containing syringe of claim 3, wherein said locking means includes a plurality of walled recesses about the periphery of said collar means to lock a portion of said key between said walls when said second tubular member is moved from said extended position to said locked and extended position.

5. The medication containing syringe of claim 1, wherein said second tubular member further includes a tapered section on said distal end thereof, said tapered section including distal and proximal ends thereon and the outer diameter of said distal end of said tapered section is substantially smaller than the outer diameter of said proximal end of said second tubular member and when said second tubular member is in said retracted position, said proximal end of said tapered section is adjacent to said distal end of said first tubular member and said distal end of said second tubular member is adjacent to said needle hub.

6. The medication containing syringe of claim 5, wherein said tapered section of said distal end of said second tubular member includes a funnel-shaped portion having an attachment means on the distal end thereof, and wherein a hollow needle sheath is removably mounted on said attachment means to protect said distal needle point.

7. The medication containing syringe of claim 1, wherein said distal end of said second tubular member is adjacent said needle hub when said second tubular member is in said retracted position and said distal end of said second tubular member extends distally of said distal needle point when said second tubular member is in said extended position.

8. The medication containing syringe of claim 1, wherein said plunger rod assembly further includes an injector assembly operatively connected to the proximal end of said first tubular member, said injector assembly including a longitudinally extending bore slidably receiving said plunger rod therein, the distal end of said plunger rod having a connecting means mounted thereon, said connector means being adapted to connect said plunger rod to a plunger means mounted in the proximal end of the medication cartridge for delivery of the medication from the medication cartridge through said hollow needle assembly upon longitudinal movement of said plunger rod toward said distal end of said first tubular member.

9. A prefilled syringe comprising:

a barrel member having distal and proximal ends and said barrel member adapted to receive a medication cartridge therein;

an elongate and hollow needle operatively mounted on said distal end of said barrel member, a first portion of said needle extends distally beyond said distal end of said barrel member to a distal needle point and a second portion of said needle extends proximally from and within said distal end of said barrel member to a proximal needle point;

a cylindrical medication cartridge positioned within said barrel member and having distal and proximal ends, said distal end including a needle pierceable diaphragm thereon and said proximal end including a movable plunger means mounted therein;

an injector assembly positioned adjacent said proximal end of said barrel member and including a plunger rod assembly reciprocally mounted thereon, said plunger rod assembly including a distal end having a connector means thereon adapted to connect said plunger rod assembly to said plunger means in said medication cartridge;

a collar operatively connected to said barrel member, said collar means including at least one pair of protrusions extending radially therefrom to form a keyway therebetween said keyway including distal and proximal ends thereon; and an elongate needle shield means having distal and proximal ends wherein said shield means is movable over said collar means between a retracted position wherein said distal needle point is exposed and an extended position wherein said distal needle point is protected, an interior surface on said shield means including at least one longitudinally extending key thereon, said key having distal and proximal ends thereon and the distance between the distal and proximal ends of said keyway is less than the distance between said distal and proximal ends of said key and said key being adapted to be movable in said keyway between said protrusions on said collar means as said shield means is moved between said retracted position and said extended position.

10. The prefilled syringe of claim 9 further including a locking member having at least one recess therein on said collar means and said key on said shield means being adapted to be rotatable into said locking member recess when said shield means is in said extended position to rotate said shield to a locked and extended position wherein said shield means is prevented from returning to said retracted position by said locking member on said collar means.

11. The prefilled syringe of claim 10, wherein said locking member recess is formed by a pair of radially extending parallel wall members having a ramp shaped side surface on at least one of said wall members and wherein said key on said shield means is rotatable over said side surface and into said locking member recess when said shield means is in said extended position.

12. The prefilled syringe of claim 9 further including at least one detent on said distal end of said shield means to contact one of said protrusions on said collar means to releasably retain said shield means in said retracted position.

13. The prefilled syringe of claim 9 further including an inwardly extending rim member on said proximal end of said shield means, said rim member being adapted to abut against said collar means to limit the distal movement of said shield means along said barrel member.

14. The prefilled syringe of claim 9 further including a funnel shaped member including a distal attachment means thereon on the distal end of said shield means and said attachment means having an outer diameter substantially smaller than the outer diameter of said proximal end of said shield means such that said attachment means is adapted to retain a needle sheath thereon.

15. A syringe, comprising:

an elongate and tubular barrel member having distal and proximal ends thereon;

an elongate and hollow needle assembly having a point on the distal end thereof and said needle assembly being operatively mounted on said distal end of said barrel member;

collar means operatively connected to said barrel member, said collar means including a longitudinally oriented keyway thereon;

a shield means having cylindrically shaped distal and proximal ends and a tapered section between said distal and proximal ends thereof and an inwardly directed and longitudinally oriented key on the inner surface thereof, said key being longer than said keyway on said collar means and wherein the outer diameter of said distal end of said shield means is smaller than the outer diameter of said proximal end;

a hollow needle sheath means closed at the distal end thereof removably mounted on said distal end of said shield means; and said shield means being longitudinally slidable relative to said collar means, said shield means being movable between a retracted position wherein said distal needle point is exposed and an extended position wherein said distal needle point is protected.

16. The syringe of claim 15 further including at least one locking member having a recess therein on the distal end of said collar means, at least one key on said shield means wherein said locking member is adapted to lock at least a portion of said key therein when said shield means is rotated from said extended position to a locked and extended position wherein said key is in said recess and said shield means is prevented from being returned to said extended position.

17. The syringe of claim 15 further including at least one pair of protrusions extending radially from said collar means and a key extending lengthwise along the interior surface of said shield means and said protrusions having a radially extending detent therebetween wherein said detent is adapted to contact said key on said shield means to releasably retain said shield means in said extended position.

18. A prefilled syringe comprising:

an elongate first tubular member having distal and proximal ends;

a hollow double ended needle assembly operatively mounted on said distal end of said first tubular member, said needle having needle points on the distal and proximal ends thereof;

a cylindrical medication cartridge adapted to contain medication therein and being received in said first tubular member, said medication cartridge including a proximal end having a movable plunger means therein and a distal end including a cap member having an orifice therein mounted thereon, said cap member including a needle piercable diaphragm therein adjacent said orifice and said diaphragm being adapted to be pierced by said proximal needle point;

an injector assembly positioned adjacent the proximal end of said first tubular member, said injector assembly including an elongate and reciprocally movable plunger rod slidably received in a longitudinally extending bore in said injector assembly, said plunger rod assembly including a connecting means on the distal end thereof adapted to connect said plunger rod assembly to said plunger means of said medication cartridge;

a collar means having distal and proximal ends, said collar means operatively connected to said first tubular member and including a plurality of spaced apart protrusions forming a keyway therebetween and a plurality of locking members extending radially therefrom, said locking members having recesses therein and being positioned adjacent to the distal surface of said protrusions on said collar means; and an elongate and tubular shield means having distal and proximal ends and at least one elongate key extending longitudinally along the internal surface of said shield means, said key having distal and proximal ends thereon and being adapted to move longitudinally through said keyway on said collar as said shield means is moved between a retracted position wherein said distal needle point is exposed and an extended position wherein said distal needle point is protected by said shield means, and the length of said key is greater than the length of said keyway on said collar means and wherein said key is further adapted to be rotatable into said recesses in said locking members on said collar means when said shield means is in said extended position to move said shield means to be locked and extended position wherein said shield means is prevented from being returned to said retracted position.

19. The prefilled syringe of claim 18 further including a radially extending detent positioned between said protrusions wherein said detent is adapted to contact at least a portion of said key as said shield means is moved between said retracted position and said extended position.

20. The prefilled syringe of claim 18, wherein said locking members are formed by pairs of wall chambers and at least one of each pair of said wall members which includes a ramp shaped side surface thereon, said wall members being positioned distally of said protrusions on said collar means such that said key is rotatable over said ramp shaped side surface and into said recess in one of said locking members.

21. A prefilled syringe comprising:
an elongate first tubular member including distal and proximal ends;
a double ended hollow needle assembly operatively mounted on said distal end of said first tubular member, said needle assembly including a needle point on the distal and proximal ends thereof;

a cylindrical medication cartridge having a medication therein and adapted to be received in said first tubular member, said medication cartridge including distal and proximal ends, said proximal end including a movable plunger means therein and said distal end including a cap means thereon, said cap means including an orifice therein and a needle pierceable diaphragm thereon, said diaphragm being adapted to be pierced by said proximal needle point;

an injector assembly operatively connected to the proximal end of said first tubular member, said injector assembly including an elongate plunger rod assembly slidably received in an elongate bore extending through said injector assembly, said plunger rod assembly having a distal end adapted to engage said plunger means in said proximal end of said medication cartridge;

collar means operatively connected to the distal end of said first tubular member and including an external surface having a plurality of spaced apart pairs of protrusions and at least one locking member thereon wherein said locking member includes at least one recess therein and being positioned distally of said protrusions on said collar means, said locking members further including a pair of radially extending wall members wherein at least one of said wall members includes a ramp shaped side surface thereon and wherein said pairs of protrusions form keyways therebetween;

an elongated and tubular shield means having distal and proximal ends and a plurality of elongate keys extending longitudinally along the interior surface of said shield means between said distal and proximal ends thereof wherein said keys are longer than said keyways on said collar means and are adapted to move longitudinally in said keyways between said protrusions as said shield means is moved between a retracted positioned wherein said distal needle point is exposed and an extended position wherein said distal needle point is protected and wherein said keys are rotationally movable over said side surface of said wall members and into said locking member to move said shield means from said extended position to a locked and extended position wherein said shield means is prevented from being returned to said retracted position;

said distal end of said shield means including a cylindrical distal portion having an outer diameter smaller than the outer diameter of said proximal end of said shield means; and a tubular needle sheath means having a closed distal end thereon said needle sheath being removably mounted about said distal portion of said shield means to protect said distal needle point.

22. A medication containing syringe comprising:
a first tubular member having distal and proximal ends and a slidable member adapted to retain a prefilled quantity of medication distally thereof;
a plunger rod assembly including a plunger rod adapted to contact said slidable member through said proximal end of said first tubular member;
a double ended hollow needle assembly including distal and proximal ends and a needle hub thereon, wherein said needle hub is operatively mounted on said distal end of said first tubular member, said needle assembly includes a distal needle point on said distal end thereof and said proximal end of said needle assembly is adapted to be in fluid communication with the medication retained distally of said slidable member and said distal needle point of said needle assembly extends distally beyond said distal end of said first tubular member;

collar means operatively connected to said first tubular member said collar means including a keyway thereon oriented longitudinally with respect to said first tubular member; and a second tubular member positioned about said first tubular member and said collar means, said second tubular member having distal and proximal ends and a key extending inwardly and longitudinally therealong, said key having distal and proximal ends and the length of said key is greater than the length of said keyway on said collar means such that said second tubular member is longitudinally movable over said first tubular member and said collar means between a retracted position wherein said distal needle point is exposed and an extended position wherein said distal needle point is protected.

23. The medication containing syringe of claim 22, wherein locking means are provided between said second tubular member and said collar means and said second tubular member is rotatably movable from said extended position to a locked and extended position wherein said second tubular member is prevented from being returned to said retracted position.

24. The medication containing syringe of claim 22, wherein said key and said keyway facilitate longitudinal and linear sliding movement of said second tubular member along said collar means and said first tubular member between said retracted and said extended positions.

25. The medication containing syringe of claim 24, wherein said key is provided on an interior surface of said second tubular member and a locking means is radially spaced apart from said keyway on said collar means and includes a plurality of walled recesses about the periphery of said collar means to lock a portion of said key between said walls when said second tubular member is moved from said extended position to said locked and extended position.

26. The medication containing syringe of claim 22, wherein said second tubular member further includes a tapered section on the distal end thereof and the outer diameter of said distal end of said tapered section is smaller than the outer diameter of said proximal end of said second tubular member and when said second tubular member is in said retracted position, said distal end of said second tubular member is adjacent to said needle hub and said distal end of said first tubular member.

27. The medication containing syringe of claim 26, wherein said tapered section on said distal end of said second tubular member includes a funnel-shaped portion having an attachment means on the distal end thereof, and wherein a hollow needle sheath is removably mounted about said attachment means to protect said distal needle point when said second tubular member is in said retracted position.

28. The medication containing syringe of claim 22, wherein said distal end of said second tubular member is adjacent said needle hub when said second tubular member is in said retracted position and said distal end of said second tubular member extends distally of said distal needle point when said second tubular member is in said extended position.

29. The medication containing syringe of claim 22, wherein said plunger rod engages said slidable member to enable said slidable member to be moved in said first tubular member in response to longitudinal movement of said plunger rod in said first tubular member.

30. A prefilled syringe comprising:

an elongate first tubular member having distal and proximal ends;

a slidable member slidably operatively mounted in said first tubular member and adapted to retain a prefilled medication distally thereof;

an injector assembly operatively associated with said first tubular member and including a reciprocally mounted plunger rod adapted to extend into said proximal end of said first tubular member and engage said slidable member to enable movement thereof;

a double ended hollow needle assembly having distal and proximal ends, wherein said needle assembly is operatively mounted on said distal end of said first tubular member and said distal end of said needle assembly includes a distal needle point thereon and said proximal end of said needle assembly is adapted to be in fluid communication with the prefilled medication contained in said first tubular member;

collar means including distal and proximal ends with a keyway extending therebetween and said collar means is operatively associated with said first tubular member; and an elongate second tubular member coaxially positioned about said first tubular member and said collar means, said second tubular member having distal and proximal ends and including an inwardly directed key thereon, said key including distal and proximal ends such that the distance between said distal and proximal ends of said key is greater than the distance between said distal and proximal ends of said collar means and said keyway and said second tubular member is longitudinally movable over said first tubular member and collar means between a retracted positioned wherein said distal needle point is exposed and an extended position wherein said distal needle point is protected.

31. The prefilled syringe of claim 30 wherein said second tubular member slidably contacts said collar means and locking means are provided between said second tubular member and said collar means.

32. The prefilled syringe of claim 31 wherein said second tubular member is slidable in said keyway on said collar means and is rotatable about said first tubular member in said extended position between a releasable extended position and a locked and extended position.

33. A syringe adapted to receive a prefilled container of medication therein, said syringe comprising:

an elongate and tubular barrel member having distal and proximal ends thereon;

a needle assembly having distal and proximal ends with a needle point on said distal end, said needle assembly being mounted in fluid communication with said distal end of said barrel member;

collar means operatively associated with said barrel member, said collar means including a keyway thereon, said keyway being longitudinally oriented with respect to said barrel member;

elongate and generally cylindrical shield means coaxially oriented with respect to said barrel member and said collar means, said shield means including distal and proximal ends and a tapered section therebetween such that the diameter of said proximal end of said shield means, said shield means further including an inner surface having an elongate key thereon, said key including distal and proximal ends thereon and the length of said key is greater than the length of said keyway on said collar means and said shield means is longitudinally slidable relative to said collar means between a retracted position wherein said needle point on said distal end of said needle is exposed and an extended position wherein said needle point is protected.

34. The syringe of claim 33 wherein said tapered section of said shield means is adjacent said distal end of said shield means such that said tapered section is adjacent said collar means when said shield means is in said retracted position and spaced apart therefrom when said shield means is in said extended position.

35. The syringe of claim 33 further including a hollow needle sheath means, said sheath means including a closed distal end and an open proximal end, said proximal end of said sheath means being sized to be removably mounted on said distal end of said shield means.

* * * * *